United States Patent
Tao et al.

(10) Patent No.: US 8,097,572 B2
(45) Date of Patent: Jan. 17, 2012

(54) RINSE-OFF PERSONAL CARE COMPOSITIONS

(75) Inventors: Binwu Tao, Beijing (CN); Timothy (Woodrow) Coffindaffer, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/686,735

(22) Filed: Jan. 13, 2010

(65) Prior Publication Data
US 2010/0179084 A1    Jul. 15, 2010

Related U.S. Application Data

(60) Provisional application No. 61/144,167, filed on Jan. 13, 2009.

(51) Int. Cl.
*A61K 7/00*    (2006.01)

(52) U.S. Cl. ........ 510/130; 510/136; 510/138; 510/156; 510/425; 510/481; 424/70.1

(58) Field of Classification Search .................. None
See application file for complete search history.

(56) References Cited

U.S. PATENT DOCUMENTS 6,114,290 A * 9/2000 Lyle et al. .................. 510/120
6,426,326 B1 7/2002 Mitra et al.

* cited by examiner

*Primary Examiner* — Necholus Ogden, Jr.
(74) *Attorney, Agent, or Firm* — Mark A. Charles

(57) ABSTRACT

The present invention relates to a cleanser composition comprising a) from about 1% to about 20% of fatty acid soap containing from about 8 to about 16 carbon atoms; b) from about 2% to about 20% of a synthetic surfactant; and c) water, wherein the composition comprises a metal ion in a level no more than a predetermined amount to provide a turbidity no higher than about 9NTU.

12 Claims, 1 Drawing Sheet

RINSE-OFF PERSONAL CARE COMPOSITIONS

CROSS REFERENCE TO RELATED APPLICATION

This application claims the benefit of U.S. Provisional Application No. 61/144,167, filed on Jan. 13, 2009.

FIELD OF THE INVENTION

The present invention relates to liquid cleansing compositions. Such compositions provide skin cleansing and/or skin moisturization and conditioning as well as attractive transparent appearance.

BACKGROUND OF THE INVENTION

Personal care compositions are well known and widely used to cleanse and moisturize skin and deliver skin benefit actives. While skin cleansing and delivery of various skin care actives or compounds that can help to condition the skin are important, it is also important that the product has a pleasant appearance and feel, both prior to and after application to deliver the consumer enjoyable in-use experience. A clear and transparent appearance of personal care products has advantages in the market since it can be attributed pureness, mildness, cleanliness, freshness or lightness to consumers. Another benefit of a clear appearance, in combination with a transparent packaging, is that the consumer is readily able to view and inspect the product.

Synthetic surfactant based cleansing products can provide clear appearance products, but have been known to have relatively weak cleansing performance and coarse lathering compared to soap-based products. While inclusion of soap in cleansing products can improve to some degree cleansing performance and/or lather properties to deliver a rich and creamy-feel lathering of synthetic surfactant based cleansing products, such inclusion of soap tends to make product appearance translucent or opaque.

Based on the foregoing, there is a need to provide a cleansing product transparent without compromising rich and creamy lathering.

None of the existing art provides all of the advantages and benefits of the present invention.

SUMMARY OF THE INVENTION

The present invention relates to a cleanser composition comprising a) from about 1% to about 20% of fatty acid soap containing from about 8 to about 16 carbon atoms; b) from about 2% to about 20% of a synthetic surfactant; and c) water, wherein the composition comprises a metal ion in a level no more than a predetermined amount to provide a turbidity no higher than about 9NTU.

This and other features, aspects, and advantages of the present invention will become evident to those skilled in the art from a reading of the present disclosure.

DETAILED DESCRIPTION OF THE INVENTION

Figure 1:
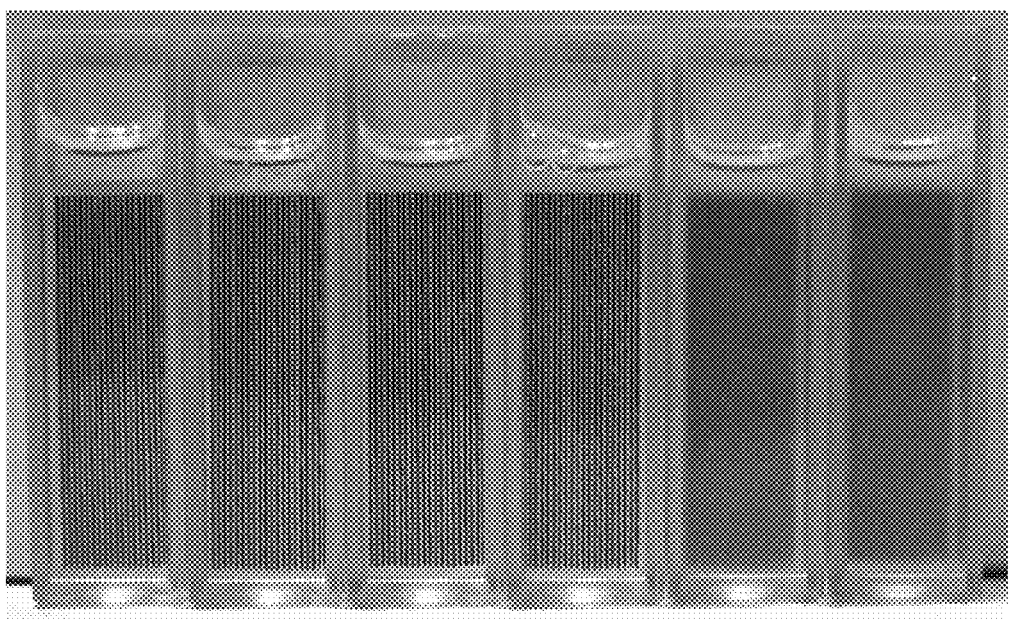
FIG. 1 is a photo showing transparency of several embodiments of the invention and one comparative example.

While the specification concludes with the claims particularly pointing and distinctly claiming the invention, it is believed that the present invention will be better understood from the following description.

All percentages and ratios used herein are by weight of the total composition and all measurements made are at 25° C., unless otherwise designated.

The term an "alkaline earth metal soap" as used herein refers to calcium soap and magnesium soap.

The term an "alkaline metal soap" as used herein refers to sodium soap and potassium soap.

The term "ambient conditions" as used herein refers to surrounding conditions under about one atmosphere of pressure, at about 50% relative humidity, and at about 25° C. unless otherwise specified.

The term "soap" as used herein includes the plural as well as the singular in terms of mixed ions and fatty acid chains unless otherwise specified.

The term "substantially free of" as used in reference to the level of a metal ion, refers to no or only trace amounts of the metal ion.

The compositions of the present invention can include, consist essentially of, or consist of, the components of the present invention as well as other ingredients described herein.

All percentages, parts and ratios are based upon the total weight of the skin care compositions of the present invention, unless otherwise specified. All such weights as they pertain to listed ingredients are based on the active level and, therefore; do not include carriers or by-products that may be included in commercially available materials, unless otherwise specified.

All publications cited herein are hereby incorporated by reference in their entirety.

The compositions of the present invention provide transparent cleansing products which can provide rich and creamy lathering as well as preferable cleansing performance.

Without being bound by theory, the transparency of the composition of the present invention may be achieved by controlling types and levels of counterions of soap in the composition. For example, fatty acid metal soap such as alkali metal or alkali earth metal soaps may result in an easy formation of soap crystals which can lead to a turbid final product. The chain length of fatty acids of the soap also may affect to turbidity of final products.

The composition of the present invention comprises metal ion which may exits in the form of soap such as alkaline metal soap and alkaline earth metal soap in a level no more than a predetermined amount to provide a turbidity no higher than about 9NTU. When the level of the metal ion is more than a predetermined amount, it may negatively affect a transparent appearance of the composition. A level of metal ion to provide a turbidity no higher than about 9NTU may vary depending on the kind of metal exiting in the composition, and can be determined and measured without undue experiment using a technology commonly used in the cosmetic and cleanser industry.

The lower limitation of metal ion in the composition of the present invention is not limited since it does not affect to the turbidity of a product. Therefore, the composition of the present invention may be substantially free of a metal ion.

In one embodiment, the composition of the present invention comprises no more than about 0.009 mol/L of a metal ion.

In one preferable embodiment, composition of the present invention comprises no more than about 0.008 mol/L of a metal ion.

The composition of the present invention is substantially transparent. Transparency of liquid compositions may be characterized by a turbidity measured by a commercially available turbidimeter such as Turbidimeter BTC-464 (Model 2100P, HACH Company, USA), as presented in the TEST METHODS.

The composition of the present invention comprises at least one fatty acid soap, at least one synthetic surfactant, and water. The compositions of the present invention optionally contain one or more skin conditioning agents. The compositions of the present invention may also include a wide variety of other ingredients. The compositions of the present invention are described in detail hereinafter.

Fatty Acid Soap

The composition of the present invention comprises fatty acid soap containing from about 8 to about 16 carbon atoms, preferably from about 10 to about 14 carbon atoms, more preferably from about 12 to about 14 carbon atoms. Fatty acid soap of a C8-C16 fatty acid is present in the composition of the present invention from about 1% to about 20%, preferably from about 3% to about 15% by weight of the composition.

The fatty acid soap in the compositions of the present invention preferably comprises an organic soap obtained using organic neutralizers such as ammonium soap, trialkanolamine soap, aminomethyl propanol soap, aminomethyl propandiol soap and tromethamine soap, more preferably triethanolamine soap and aminomethyl propanol soap.

Synthetic Surfactants

The composition of the present invention comprises a synthetic surfactant. The synthetic surfactant is present in the composition of the present invention from about 2% to about 20%, preferably from about 3% to about 15%, most preferably from about 4% to about 10% by weight of the composition. The synthetic surfactant can be selected from anionic, nonionic, amphoteric and ampholytic surfactants. Such surfactants are well known to those skilled in the cosmetic and cleanser manufacturing field.

Anionic Surfactants

A wide variety of anionic surfactants are useful herein. Nonlimiting examples of anionic surfactants include the alkoyl isethionates, and the alkyl and alkyl ether sulfates. The alkoyl isethionates typically have the formula RCO—OCH$_2$CH$_2$SO$_3$M wherein R is alkyl or alkenyl of from about 10 to about 30 carbon atoms, and M is a non-metal water-soluble cation such as ammonium, trialkanolamine, and aminomethyl propanol. Nonlimiting examples of these isethionates include those alkoyl isethionates such as ammonium cocoyl isethionate.

The alkyl and alkyl ether sulfates typically have the respective formulae ROSO$_3$M and RO(C$_2$H$_4$O)$_x$SO$_3$M, wherein R is alkyl or alkenyl of from about 10 to about 30 carbon atoms, x is from about 1 to about 10, and M is non-metal water-soluble cation such as ammonium, trialkanolamine, and aminomethyl propanol. Another suitable class of anionic surfactants is water-soluble salts of organic, sulfuric acid reaction products of the general formula R$_1$—SO$_3$-M, wherein R$_1$ is chosen from the group consisting of a straight or branched chain, saturated aliphatic hydrocarbon radical having from about 8 to about 24, preferably about 10 to about 16, carbon atoms; and M is a cation which is not an alkaline metal or alkaline earth metal cation. Still other anionic synthetic surfactants include the class designated as succinamates, olefin sulfonates having about 12 to about 24 carbon atoms, and b-alkyloxy alkane sulfonates. An example of these materials is ammonium lauryl sulfate.

Other anionic surfactants include phosphates such as monoalkyl, dialkyl, and trialkylphosphate salts.

Other anionic surfactants include alkanoyl sarcosinates corresponding to the formula RCON(CH$_3$)CH$_2$CH$_2$CO$_2$M wherein R is alkyl or alkenyl of about 10 to about 20 carbon atoms, and M is a non-metal water-soluble cation such as ammonium and trialkanolamine. An example is ammonium lauroyl sarcosinate.

Nonionic Surfactants

A wide variety of nonionic surfactants are useful herein. Among the nonionic surfactants that are useful herein are the condensation products of sorbitol with a fatty acid. Nonlimiting examples include the Tweens, Spans, and the Polysorbates.

Other useful nonionic surfactants include the condensation products of alkylene oxides with fatty acids (i.e. alkylene oxide esters of fatty acids). These materials have the general formula RCO(X)$_n$OH wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants. A preferred polyhydroxy fatty acid amide surfactant is coconut alkyl N-methyl glucoside amide. Non-limiting examples of suitable nonionic surfactants include: polyethylene glycol 20 sorbitan monolaurate (Polysorbate 20), polyethylene glycol 5 soya sterol, steareth-20, steareth-21, ceteareth-20, ceteareth-12, PPG-2 methyl glucose ether distearate, ceteth-10, Polysorbate 80, cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, diethanolamine cetyl phosphate, glyceryl stearate, PEG-100 stearate, and mixtures thereof. Preferred nonionic surfactants are those selected from the group consisting of steareth-21, ceteareth-20, ceteareth-12, Tween-60, Tween-80, sucrose cocoate, steareth-100, PEG-100 stearate, PEG-1000 stearate, and mixtures thereof.

Amphoteric Surfactants

The term "amphoteric surfactant," as used herein, is also intended to encompass zwitterionic surfactants, which are a subset of amphoteric surfactants.

A wide variety of amphoteric surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992). Nonlimiting examples amphoteric surfactants are those selected from the group consisting of betaines, sultaines, hydroxysultaines, alkyliminoacetates, iminodialkanoates, aminoalkanoates, and mixtures thereof. Preferred amphoteric surfactants include lauramidopropyl betaine, cetyl dimethyl betaine (i.e. cetyl betaine), cocoamidopropyl betaine, cocoamidopropyl hydroxy sultaine, or mixtures thereof.

Water

The compositions of the present invention comprise water.

Optional Ingredients

Skin Conditioning Agents

Optionally, the composition of the present invention can further comprise a skin conditioning agent. These agents may be selected from humectants, emollients, and mixtures thereof.

A variety of humectants can be optionally employed in the present compositions. Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin.

When the conditioning agent is an emollient it may be selected from hydrocarbons, fatty acids, fatty alcohols, esters and mixtures thereof.

When used, the amount of skin-condition agent is present in the composition from about 0.1% to about 20%, more preferably from about 1% to about 15%, and most preferably from about 3% to about 8%, by weight of the composition.

Thickeners

The compositions of the present invention, in some embodiments, may further include one or more thickeners (polymeric or inorganic). When present, the thickeners are preferably incorporated in the present compositions at a level of at least about 0.01%, more preferably at least about 0.05%, and still more preferably at least about 0.1%, by weight of the composition. It can often be useful to blend different thickeners together to generate an optimal stability and rheology profile.

Non-limiting examples of polymeric thickeners useful herein include carboxylic acid polymers such as the carbomers (such as those commercially available under the tradename CARBOPOL® 900 series from B.F. Goodrich; e.g., CARBOPOL® 954) and the Luvigel series from BASF. Other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerythritol. These copolymers are known as acrylates/$C_{10-30}$ alkyl acrylate crosspolymers and are commercially available as CARBOPOL® 1342, CARBOPOL® 1382, CARBOPOL® Ultrez 21, CARBOPOL® Ultrez 20, CARBOPOL® Ultrez 10, PEMULEN® TR-1, and PEMULEN® TR-2, from B.F. Goodrich.

Other non-limiting examples of polymeric thickeners include crosslinked polyacrylate polymers including both cationic and nonionic polymers.

Still other non-limiting examples of polymeric thickeners include the polyacrylamide polymers, especially nonionic polyacrylamide polymers including substituted branched or unbranched polymers. Other polyacrylamide polymers useful herein include multi-block copolymers of acrylamides and substituted acrylamides with acrylic acids and substituted acrylic acids. Commercially available examples of these multi-block copolymers include HYPAN® SR150H, SS500V, SS500W, SSSA100H, from Lipo Chemicals, Inc., (Patterson, N.J.).

Another non-limiting class of polymeric thickeners useful herein is polysaccharides. Non-limiting examples of polysaccharide gelling agents include those selected from cellulose, and cellulose derivatives. Preferred among the alkyl hydroxyalkyl cellulose ethers is the material given the CTFA designation hydroxyethylcellulose, which is sold under the trade name of Natrosol 250HHR from Hercules Incorporated. Another useful polysaccharides include scleroglucans which are a linear chain of (1-3) linked glucose units with a (1-6) linked glucose every three units, a commercially available example of which is CLEAROGEL™ CS11 from Michel Mercier Products Inc. (Mountainside, N.J.).

Another non-limiting class of polymeric thickeners useful herein is the gums. Non-limiting examples of gums useful herein include hectorite, hydrated silica, xantham gum, and mixtures thereof.

Yet another non-limiting class of polymeric thickeners useful herein is the modified starches. Acrylate modified starches such as WATERLOCK® from Grain Processing Corporation may be used. Hydroxypropyl starch phosphate, trade name STRUCTURE XL® from National Starch is another example of a useful modified starch, and other useful examples include ARISTOFLEX® HMB (Ammonium Acrylodimethyltaruate/Beheneth-25 Methacrylate Crosspolymer) from Clariant and cationic stabylens.

Still another non-limiting class of thickeners useful herein is the inorganic synthetic layered silicate, Laponite series, such as Laponite RD, Laponite XLG and Laponite D.

Exfoliating Agents

The present compositions can optionally further comprise exfoliating agents derived from a wide variety of particulate materials including those derived from inorganic, organic, natural, and synthetic sources.

The particulate exfoliating agents of the present invention, when present, are typically utilized at a level of from about 0.1% to about 8%, preferably from about 0.25% to about 6%, by weight of the composition. These materials include those of water-insoluble particles, both inorganic and polymeric particles Non-limiting examples of those particles are water-insoluble clay, iron oxide, jojoba seed powder, kaolin, mica, polybutylene, polyethylene, polyisobutylene, polymethylstyrene, polypropylene, polystyrene, polyurethane, nylon, teflon (i.e. polytetrafluoroethylene) and mixtures thereof.

Among the preferred water-insoluble, particulate materials useful as exfoliating agents herein are the synthetic polymeric particles. Synthetic polymeric particles useful in the present invention are selected from the group consisting of polybutylene, polyethylene, polyisobutylene, polymethylstyrene, polypropylene, polystyrene, polyurethane, oxidized derivatives thereof, nylon, teflon, and mixtures thereof. Non-limiting examples of suitable exfoliating agents include oxidized polyethylene beads commercially available as A-C Oxidized Polyethylene beads from Honeywell and ACCUSCRUB™ beads from Accutech, LLC.

Composition Preparation

The composition of the present invention is generally prepared by conventional methods such as are known in the art of making rinse-off cleansing compositions. Such methods typically involve mixing of the ingredients in one or more steps to a relatively uniform state, with or without heating, cooling, application of vacuum, and the like.

Product for Use

In preferred embodiments, the composition of the present invention is substantially transparent liquid having turbidity no more than about 9NTU with or without color. In one preferred embodiment, the composition of the present invention is transparent having turbidity no more than about 7NTU.

In another preferred embodiment, the composition of the present invention has a pH in the range of 7.5-9.0, preferably in the range of 7.8-8.7, still more preferable in the range of 8.0-8.3 which can provide a mild cleanser product but still have excellent cleaning performance.

In another preferred embodiment, the composition of the present invention contains visible particles and/or bead providing a unique appearance.

In another preferred embodiment, the composition of the present invention can be packaged in a transparent container through which consumers can view and inspect the composition.

In some of the embodiments, the composition of the present invention may further comprise a component selected from the group consisting of skin actives, skin conditioning agents, and thickening agents.

Test Methods

Salt Measurement

The salt in the composition may be measured according to an Inductively Coupled Plasma-Atomic Emission Spectrometry (ICP-AES) method such as Chinese National Standard GB/T 5750.6-2006 ICP-AES test method using a commercially available Inductively Coupled Plasma-Atomic Emission Spectrometry. As an example, a salt level herein can be measured by iCAP 6300 Spectrometer, from Thermo Electron Corp., US.

Turbidity Measurement

Turbidity in a solution can be determined by measuring ratio nephelometric signal)(90°) which is ratio of the scattered 90° and transmitted light signal. As an example, turbidity herein can be measured by HACH 2100P Turbidimeter from HACH Company, USA.

The measurement is conducted at a temperature of approximately 25° C. The test range of the turbidity can be set automatic mode. The sample is filled into a (Height×width) 60.0×25 mm (2.36×1 in) Borosilicate glass vial (about 15 mL/0.5 oz) with a screw cap. The sample cell in a fixed place is held for more than 2 hours to let the gas/bubbles out, and wiped. After that, a thin film of silicone oil is applied to the outside of the sample cell, which is wiped with soft cloth to obtain an even film over the entire surface. The sample vial is put into the test hole of the HACH 2100P Turbidimeter, and a turbidity of the sample is measured.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

TABLE 1

| Ingredients | EX 1 | EX 2 | EX 3 | EX 4 | EX 5 | EX 6 | EX 7 |
|---|---|---|---|---|---|---|---|
| Mix A | | | | | | | |
| Hydroxyethylcellulose | 1.20 | 1.20 | — | 1.0 | 0.8 | — | 1.1 |
| Aculyn 88 *1 | — | — | 2.0 | — | — | 2.5 | — |
| Water | q.s. to 100 | q.s. to 100 | q.s. to 100 | q.s. to 100 | q.s. to 100 | q.s. to 100 | q.s. to 100 |
| Disodium EDTA | 0.05 | 0.05 | 0.10 | 0.05 | — | — | 0.05 |
| Mix B | | | | | | | |
| Glycerin | 8.00 | 8.00 | 4.00 | 5.00 | 6.00 | 8.00 | 6.00 |
| PEG-7M | 0.10 | 0.10 | 0.05 | 0.10 | — | — | 0.10 |
| Triethanolamine | 7.00 | 9.00 | 9.00 | — | 7.5 | 11.5 | 8.00 |
| Aminomethyl propanol | — | — | — | 3.5 | — | — | — |
| Mix C | | | | | | | |
| Lauric acid | 2.00 | 2.50 | 2.00 | 4.50 | 2.00 | 2.50 | 2.00 |
| Myristic acid | 6.00 | 7.50 | 5.00 | 4.50 | 6.00 | 7.50 | 5.00 |
| Palmitic acid | — | — | 1.00 | — | — | — | — |
| PEG-150 Pentaerythrityl tetrastearate | 0.50 | 0.50 | 0.50 | 0.50 | — | — | 1.00 |
| Mix D | | | | | | | |
| Lauramidopropyl betaine | 7.00 | 10.00 | 6.00 | 4.00 | 15.0 | 9.0 | — |
| Cocoamidpropyl betaine | — | — | — | — | — | — | 7.50 |
| Glydant Plus Liquid *2 | 0.40 | 0.40 | 0.30 | 0.20 | 0.40 | 0.30 | 0.30 |
| Mix E | | | | | | | |
| Menthol | 0.10 | 0.10 | — | 0.10 | — | — | — |
| Perfume | 0.30 | 0.30 | 0.30 | 0.30 | 0.30 | 0.30 | 0.30 |
| Pigment | — | 0.008 | — | — | — | — | — |

*1 Aculyn 88: Acrylate/Streareth-20 methacrylate Crosspolymer. Available from Rohm and Haas
*2 Glydant Plus Liquid: DMDM Hydantoin, Iodopropynyl butylcarbamate, 1,3 butylene glycol in water. Available from Lonza Inc.

The compositions of all the Examples can be made as follows. Mixes A and B are agitated until they are well dispersed into the water, then the obtained mixture is heated to 75° C. to be a clear gel. A neutralizer (triethanolamine or aminomethyl propanol) is added into the clear gel. Mix C is heated until 75° C., and the heated Mix C is added into the clear gel obtained above. The obtained mixture is mixed until it becomes clear, and the heat is removed. During cooling the mixture down, Mix D is added into it and mixed. When the temperature is below 40° C., Mix E and a pigment or dye is added if needed.

Metal ion levels in the compositions of Examples 1 and 2 were measured according to Chinese National Standard GB/T 5750.6-2006, ICP-AES test method using iCAP 6300 Spectrometer. Examples 1 and 2 contained 0.076% Na$^+$ ion, respectively. Other metal ions except Na$^+$ ion alkali exist as trace.

Examples 8-12 and Comparative Example 1

Compositions of Examples 8-12 and Comparative Example 1 were prepared by adding a different amount of 20% NaCl solution into Example 1 composition. The amount of Na$^+$ ion in each composition was calculated from the amount of NaCl solution added, and is shown in Table 2 below.

Turbidities of Examples 1 and 8-12, and Comparative Example 1 were measured according to TURBIDITY MEASUREMENT using HACH 2100P Turbidimeter (HACH Company, USA), and are also shown in Table 2. The test range of the turbidity was set to automatic mode. Each composition of Examples 8-12 and Comparative Example 1 was placed in a 4 ml clear cell with a vertical line background. A photo of the cells was taken, and is provided in FIG. 1.

TABLE 2

|  | EX 1 | EX 8 | EX 9 | EX 10 | EX 11 | EX 12 | Com. EX 1 |
|---|---|---|---|---|---|---|---|
| Na$^+$ (wt %) | 0.076 | 0.116 | 0.115 | 0.183 | 0.195 | 0.206 | 0.210 |
| Na$^+$ (mol/L) | 0.00033 | 0.00050 | 0.00050 | 0.00080 | 0.00085 | 0.00090 | 0.00091 |
| Turbidity (NTU) | 1.14 | 1.28 | 2.11 | 4.18 | 6.14 | 7.84 | 9.62 |
| *RSD | 3.82% | 1.96% | 1.93% | 0.63% | 2.22% | 0.27% | 1.30% |

*RSD: Relative Standard Deviation

Examples 13-18

Examples 13-18 were prepared by adding a different amount of 20% KCl solution into Example 2 composition. The amount of K$^+$ ion in each composition was calculated from the amount of KCl solution added, and is shown in Table 3 below. Turbidities of Examples 2 and 13-18 were measured according to TURBIDITY MEASUREMENT using HACH 2100P Turbidimeter (HACH Company, USA), and are also shown in Table 3. The test range of the turbidity was set to automatic mode.

TABLE 3

|  | EX 2 | EX 13 | EX 14 | EX 15 | EX 16 | EX 17 | EX 18 |
|---|---|---|---|---|---|---|---|
| K$^+$ (wt %) | 0.130 | 0.235 | 0.339 | 0.365 | 0.376 | 0.381 | 0.392 |
| K$^+$ (mol/L) | 0.00033 | 0.00060 | 0.00087 | 0.00094 | 0.00096 | 0.00098 | 0.001001 |
| Turbidity (NTU) | 0.92 | 1.25 | 3.31 | 5.52 | 7.64 | 7.67 | 8.38 |
| RSD | 2.17% | 1.60% | 0.60% | 0.55% | 0.26% | 0.49% | 0.21% |

*The potassium level in Example 2 was translated from sodium level measured above by the chemical equivalent.

It is understood that the foregoing detailed description of examples and embodiments of the present invention are given merely by way of illustration, and that numerous modifications and variations may become apparent to those skilled in the art without departing from the spirit and scope of the invention; and such apparent modifications and variations are to be included in the scope of the appended claims.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleanser composition comprising:
   a) from about 1% to about 20% of free fatty acid soap containing from about 8 to about 16 carbon atoms, wherein the free fatty acid soap comprises an organic soap selected from the group consisting of aminomethyl propanol soap, aminomethyl propandiol soap, trimethamine soap, and mixtures thereof;
   b) from about 2% to about 20% of a synthetic surfactant; and
   c) water,
   wherein the composition comprises a metal ion in a level no more than a predetermined amount to provide a turbidity no higher than about 9NTU.

2. The composition according to claim 1, wherein said metal ion is selected from the group consisting of an alkaline metal, an alkaline earth metal, and a mixture there of.

3. The composition according to claim 1, wherein said synthetic surfactant is selected from the group consisting of non-ionic surfactants, anionic surfactants, amphoteric surfactants and mixtures thereof.

4. The composition according to claim 1, wherein said composition is a liquid form.

5. The composition according to claim 1, wherein said composition comprises no more than about 0.0009 mol/L of said metal ion.

6. The composition according to claim 1, wherein said composition comprises no more than about 0.008 mol/L of said metal ion.

7. The composition according to claim 1, wherein said composition is substantially free from said metal ion.

8. The composition according to claim 1, wherein said composition has a turbidity no more than about 6NTU.

9. The composition according to claim 1, wherein said composition has a pH in the range of from about 7.5 to about 9.0.

10. The composition according to claim 1, wherein said composition further comprises at least one compound selected from the group consisting of skin conditioning agents, Exfoliating agents, thickeners and mixtures thereof.

11. The composition according to claim 1, wherein said composition further comprises a visible particle.

12. The composition according to claim 1, wherein said composition is packaged in a transparent container.

* * * * *